(12) United States Patent
Lee (10) Patent No.: US 9,159,299 B2
(45) Date of Patent: Oct. 13, 2015

(54) COMPENSATED METHOD OF DISPLAYING BASED ON A VISUAL ADJUSTMENT FACTOR

(75) Inventor: John Jong-Suk Lee, Waterloo (CA)

(73) Assignee: BlackBerry Limited, Waterloo (CA)

( * ) Notice: Subject to any disclaimer, the term of this patent is extended or adjusted under 35 U.S.C. 154(b) by 221 days.

(21) Appl. No.: 13/272,596

(22) Filed: Oct. 13, 2011

(65) Prior Publication Data

US 2013/0093796 A1    Apr. 18, 2013

(51) Int. Cl.
| | |
|---|---|
| G09G 5/00 | (2006.01) |
| G09G 5/14 | (2006.01) |
| G09G 3/00 | (2006.01) |
| A61B 3/00 | (2006.01) |

(52) U.S. Cl.
CPC ............... *G09G 5/14* (2013.01); *G09G 3/003* (2013.01); *A61B 3/0041* (2013.01); *G09G 2300/023* (2013.01); *G09G 2380/08* (2013.01)

(58) Field of Classification Search
CPC .......... H04N 13/0018; H04N 13/0022; G09G 2320/06; G09G 2320/0686; G09G 2320/10; G09G 2320/0261; G02B 27/22; G02B 27/2221; G02B 2027/0178; G02B 21/008
USPC ............................ 345/4–6, 7–9, 32, 619, 690
See application file for complete search history.

(56) References Cited

U.S. PATENT DOCUMENTS

| | | | |
|---|---|---|---|
| 7,205,959 B2* | 4/2007 | Henriksson | 345/4 |
| 7,619,585 B2* | 11/2009 | Bell et al. | 345/9 |
| 8,154,473 B2* | 4/2012 | Engel et al. | 345/4 |
| 8,427,393 B2* | 4/2013 | Nakazaki et al. | 345/5 |
| 8,432,411 B2* | 4/2013 | Bell et al. | 345/589 |
| 8,436,873 B2* | 5/2013 | Gao | 345/634 |
| 2004/0108984 A1 | 6/2004 | Ogasawara | |
| 2005/0041040 A1* | 2/2005 | Fukuda et al. | 345/619 |
| 2005/0052341 A1 | 3/2005 | Henriksson | |
| 2011/0157180 A1* | 6/2011 | Burger et al. | 345/428 |
| 2012/0262477 A1* | 10/2012 | Buchheit | 345/619 |

OTHER PUBLICATIONS http://forums.dpreview.com/forums/read.asp?forum=1014&message=32459447 Digital Photography Review Forums—Lens Distortion Correction—post #32459447 dated Jul. 21, 2009 (2 pages).
http://www.northlight-images.co.uk/article_pages/focus_magic.html Focus Magic—because you don't always get it right—Oct. 2005 (3 pages).

(Continued)

*Primary Examiner* — Kent Chang
*Assistant Examiner* — Herbert L Hagemeier
(74) *Attorney, Agent, or Firm* — Todd A. Keeler; Borden Ladner Gervais LLP (57) ABSTRACT

A method and a device for displaying images on a display based on a visual adjustment factor related to a user's prescription eyewear are provided. The display includes a front display plane and a back display plane and for each of a plurality of image elements of an image, a respective version of the image element is displayed on each of the front display plane and the back display plane based on the visual adjustment factor such that the respective versions of the image element differ in at least one of line weight and transparency.

19 Claims, 7 Drawing Sheets

(56) References Cited

OTHER PUBLICATIONS http://spie.org/x35997.xml?ArticleID=x35997 Characterization and correction of abnormal optics in the human eye—Seth Pantanelli, Geunyoung Yoon, and Ramkumar Sabesan—Jul. 21, 2009 (4 pages).
http://shenews.projo.com/2009/08/eyeglasses-whos.html The Providence Journal—Subterranean Blog—Eyeglasses whose focus you adjust on the fly are available now—Aug. 10, 2009 (3 pages).
Miller, R. J.,: "Pitfalls in the conception, manipulation, and measurement of visual accommodation", Human Factors Feb. 1990 LNKD-PUBMED: 2198224, vol. 32, No. 1, Feb. 1990, pp. 27-44, XP9157743.
Extended European Search Report for European Patent Application No. 11185115.0, dated Apr. 4, 2012, 7 pages.
Examination Report dated Sep. 2, 2014 from corresponding European Patent Application No. 11185115.0.
K. J. Mackenzie et al., "Accommodation to multiple-focal-plane displays: Implications for improving stereoscopic displays and for accommodation control", Journal of Vision, Jul. 26, 2010, pp. 1-20, vol. 10, No. 8.
F M Toates, "Accommodation function of the human eye", Physiological Reviews, Oct. 1, 1972, pp. 828-863, vol. 52, No. 4, US.
Examiner's Report dated Jun. 29, 2015, issued in respect of corresponding Canadian Patent Application No. 2,792,182.
Pamplona et al., "Interactive display for estimating refractive errors and focal range", In SIGGRAPH 2010, 77, pp. 1-8, 2010.

* cited by examiner

COMPENSATED METHOD OF DISPLAYING BASED ON A VISUAL ADJUSTMENT FACTOR

FIELD OF THE INVENTION

The present disclosure relates to visual displays.

BACKGROUND

Many people require reading glasses, prescription eyewear, including contact lenses, or other type of corrective eyewear in order to be able to clearly view text or other images. This includes images and/or text displayed on the display of a device, such as the screen of a computer monitor or handheld mobile device.

However, there are instances where a user of a device may not be wearing their corrective eyewear and, therefore, the user may perceive the images displayed on the device to be blurry without the correction to focal length provided by their corrective eyewear.

BRIEF DESCRIPTION OF THE DRAWINGS

Embodiments of the present disclosure will now be described in greater detail with reference to the accompanying drawings, in which.

DETAILED DESCRIPTION

In the following detailed description of sample embodiments, reference is made to the accompanying drawings, which form a part hereof, and in which is shown by way of illustration specific sample embodiments in which the present invention may be practised. These embodiments are described in sufficient detail to enable those skilled in the art to practice the invention, and it is to be understood that other embodiments may be utilized and that logical, mechanical, electrical, and other changes may be made without departing from the scope of the invention. The following detailed description is, therefore, not to be taken in a limiting sense, and the scope is defined by the appended claims.

According to one aspect of the present disclosure, there is provided a method for displaying using a display having a front display plane and a back display plane, the method comprising: for each of a plurality of image elements of an image, displaying a respective version of the image element on each of the front display plane and the back display plane based on a visual adjustment factor such that the respective versions of the image element differ in at least one of line weight and transparency.

In some embodiments, the difference in at least one of line weight and transparency between the respective versions of the image element displayed on the front display plane and the back display plane based on the visual adjustment factor sets the visual focal length to the display to one of the front display plane and the back display plane while the respective version of the image element displayed on the other one of the front display plane and the back display plane is perceptible.

In some embodiments, the method further comprises adjusting light intensity of at least one of the front display plane and the back display plane based on the visual adjustment factor.

In some embodiments, the visual adjustment factor comprises eye correction prescription information.

In some embodiments, displaying a respective version of the image element on each of the front display plane and the back display plane based on a visual adjustment factor such that the respective versions of the image element differ in at least one of line weight and transparency comprises: displaying a respective version of the image element on each of the front display plane and the back display plane, such that the visual focal length to the display is set to the front display plane of the display for eye correction prescription information indicative of hyperopia; and displaying a respective version of the image element on each of the front display plane and the back display plane such that the visual focal length to the display is set to the rear display plane of the display for eye correction prescription information indicative of myopia.

In some embodiments, the eye correction prescription information comprises a spherical correction, and the method further comprises: determining a focal length correction based on the spherical correction; and displaying the respective image elements of the front display plane and the back display plane of the display with relative scaling with respect to one another based on the focal length correction and a distance between the display and the user's eyes.

In some embodiments, the method further comprises determining the distance between the display and a user's eyes by measuring the distance with a measuring device.

In some embodiments, the method further comprises prompting for entry of the eye correction prescription information.

In some embodiments, displaying a respective version of the image element on each of the front display plane and the back display plane based on a visual adjustment factor such that the respective versions of the image element differ in at least one of line weight and transparency corresponds to operating in a compensated display mode, the method further comprising automatically operating in the compensated display mode responsive to at least one of: a time of day; and an elapsed period of inactivity of the display.

In some embodiments, displaying a respective version of the image element on each of the front display plane and the back display plane based on a visual adjustment factor such that the respective versions of the image element differ in at least one of line weight and transparency corresponds to operating in a compensated display mode, the method further comprising switching between the compensated display mode and at least one other display mode responsive to user input.

According to another aspect of the present disclosure, there is provided a device comprising: a display having a front display plane and a back display plane; and a display controller that, in a compensated display mode, is configured to control the display to display, for each of a plurality of image elements of an image, a respective version of the image element on each of the front display plane and the back display plane of the display based on a visual adjustment factor such that the respective versions of the image element differ in at least one of line weight and transparency.

In some embodiments, the display controller is configured to control the display to display the respective versions of the image elements such that the difference in at least one of line weight and transparency between the respective versions of the image element displayed on the front display plane and the back display plane based on the visual adjustment factor sets the visual focal length to the display to one of the front display plane and the back display plane while the respective version of the image element displayed on the other one of the front display plane and the back display plane is perceptible.

In some embodiments, the display controller is further configured to adjust light intensity of at least one of the front display plane and the back display plane based on the visual adjustment factor.

In some embodiments, the visual adjustment factor comprises eye correction prescription information.

In some embodiments, the display controller is configured to: control the display to adjust at least one of the line weight and transparency of the respective versions of the image elements of the front display plane and the back display plane such that the visual focal length to the display is set to the front display plane for eye correction prescription information indicative of hyperopia; and control the display to adjust at least one of the line weight and transparency of the respective versions of the image elements of the front display plane and the back display plane such that the visual focal length to the display is set to the rear display plane for eye correction prescription information indicative of myopia.

In some embodiments, the eye correction prescription information comprises a spherical correction and the display controller is further configured to: determine a focal length correction based on the spherical correction; and control the display to display the respective versions of the image elements of the front display plane and the back display plane with relative scaling with respect to one another based on the focal length correction and a distance between the display and the user's eyes.

In some embodiments, the device further comprises a distance measuring sensor configured to measure the distance between the display and a user's eyes.

In some embodiments, the display controller is further configured to prompt for entry of the eye correction prescription information.

In some embodiments, the display controller is further configured to automatically operate in the compensated display mode responsive to at least one of: a time of day; and an elapsed period of inactivity of the device.

In some embodiments, the display controller is further configured to switch between the compensated display mode and at least one other display mode responsive to user input.

According to another aspect of the present disclosure, there is provided a mobile device that includes a device as described above or detailed below.

Imperfections in the cornea, retina or other structures of the eye result in imperfections or blurriness when viewing images. To compensate for these imperfections, corrective eyewear, such as eye glasses and contact lenses, are typically worn on, or in close proximity to, the eyes in order to counteract the effects of the eye imperfections. Some examples of conditions associated with eye imperfections include hyperopia, which is commonly known as "far sightedness", in which a person is able to focus on relatively distant images but has difficulty clearly focusing on relatively near images, and myopia, which is commonly known as "near sightedness", in which a person is able to focus on relatively near images but has difficulty clearly focusing on relatively distant images.

In some cases, a person's eyes may have a relatively equal distortion of the cornea in all meridians of the cornea, which is commonly called a spherical defect/deformation that can generally be compensated for by a spherical correction that corrects a refractive error of the eye with a single convergent (for far sightedness) or divergent (for near sightedness) refractive power in all meridians.

In some cases, a person's eyes may also have a cylindrical defect/deformation, which is commonly referred to as astigmatism and which may be compensated for with a cylindrical correction that corrects the astigmatic refractive error of the eye by adding or subtracting refractive power cylindrically in a meridian of the eye specified by a prescribed axis. In these cases, the axis indicates the angle in degrees of one or two major meridians the prescribed cylindrical refractive power is in. Typically, in an eye prescription, which major meridian is referenced is indicated by the cylindrical correction being in plus or minus notation. The axis is typically measured on an imaginary semicircle with a horizontal baseline that starts with zero degrees in the 3 o'clock (or east) direction, and increases to 180 degrees in a counter-clockwise direction.

Due to eye imperfections, such as those discussed above, user's of, for example, a mobile device having an image display, may be unable to clearly view images displayed on the image display without the aid of corrective eyewear. The corrective eyewear works by providing a focal length correction that compensates, at least partially, for focal length errors introduced by the eye imperfections. However, as noted above, the user of a mobile device may not always be wearing their corrective eyewear, for example, early in the morning upon waking, and therefore may not be able to clearly view images on the display.

Some embodiments of the present disclosure provide methods and devices for displaying images in a manner that compensates, at least partially, for eye imperfections of a user. In some embodiments, the focal length to a display is adjusted to a front display plane or a back display plane of the display by displaying a respective version of an image element on each of the front display plane and the back display plane of the display based on a visual adjustment factor that, in some embodiments, includes eye correction prescription information, such that the respective versions of the image element displayed on the front display plane and the back display plane differ in at least one of line weight and transparency. Displaying image elements in this manner can potentially allow a user to view images on a display when not wearing their corrective eyewear, as their eyes may be prompted to attempt to focus on the image elements on one of the display planes while the image elements on the other display plane are also perceptible. An image element is a part of an image and may, for example, be text, shapes or any other visual part of an image that is displayed.

It should be understood that the term respective image element is used herein to indicate that each display plane displays its own version of an image element that differ from one another in at least one of line weight and transparency.

The terms front and back are used herein to be consistent with a user's point of view as a user uses the display in an ordinary way.

It should be understood that, while the term display plane is used herein to refer to the display surface on which image elements are displayed, the surface, though substantially planar, may have some curvature to it and need not be strictly planar.

It should also be understood that the term visual adjustment factor, as used herein, is intended to encompass factors that impact the visual perception of a displayed image. While eye correction prescription information is provided as an example of information upon which a visual adjustment factor may, at least in part, be based, it is to be understood that other factors are contemplated.

Illustrative embodiments of the present disclosure will now be described with reference to FIGS. 1 to 7. It is to be understood that these embodiments are described as illustrative examples only and are not to be construed as limiting.

Figure 1:
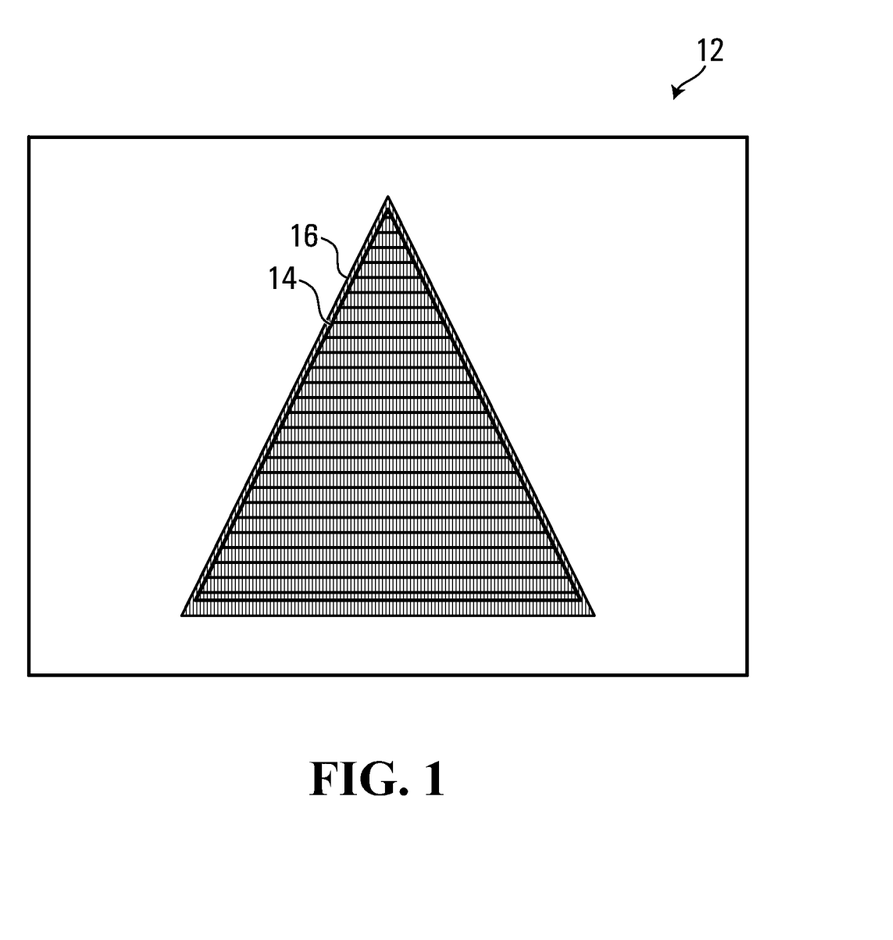
FIG. 1 is a diagram of an image display in accordance with an embodiment of the present disclosure.

FIG. 1 is a diagram of an image display 12 in accordance with an embodiment of the present disclosure. Display 12 includes a front display plane 11A and a back display plane 11B (see FIG. 2B). In FIG. 1, display 12 is shown as currently displaying a triangular image that is displayed by displaying respective triangular image elements 14 and 16 on the front display plane 11A and the back display plane 11B of display 12. Respective triangular image elements 14 and 16 have at least one differing image property such that the visual focal length to the display 12 is set to one of the front display plane 11A and the back display plane 11B while the respective image element of the other one of the front display plane 11A and the back display plane 11B is perceptible. For example, by varying at least one of the line weight, transparency and light intensity of one of the image elements 14 and 16 relative to the other, a user's eyes may be "tricked" into focusing on either a) the image element 14 displayed on the front display plane 11A, while the eye still perceives the image element 16 displayed on the back display plane 11B, or b) the image element 16 displayed on the back display plane 11B, while the eye still perceives the image element 14 displayed on the front display plane 11A.

By "tricking" the eye to focus on the relatively more distant back display plane 11B, while still perceiving images on the relatively nearer front display plane 11A, the display may at least partially compensate for a myopia (near sighted) condition. Similarly, "tricking" the eye to focus on the relatively nearer front display plane 11A, while still perceiving images on the relatively more distant back display plane 11B may at least partially compensate for a hyperopia (far sighted) condition.

Further details of embodiments for compensating for hyperopia and myopia will now be discussed with reference to FIGS. 2A, 2B, 3A and 3B.

Figure 2A:
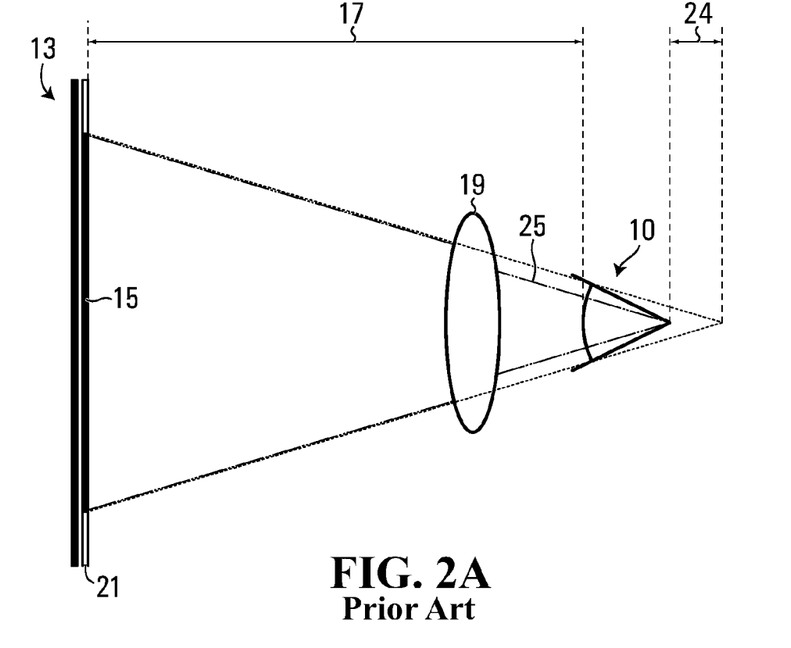
FIG. 2A is a profile view of a conventional image display and a prescription lens configured to compensate for hyperopia.

FIG. 2A is a profile view of a conventional image display 13 and a convergent prescription lens 19 configured to compensate for hyperopia. The image display 13 has a single display plane 21 on which an image 15 is displayed. When a user, whose eye is generally indicated at 10 in FIG. 2A, views the image 15 displayed on the display plane 21 of display 13 at a distance 17 from the display, the imperfections in the user's eye 10 that cause hyperopia cause light from display 13 to be improperly focuses at a distance 24 behind the user's retina, rather than properly focusing the light on the retina at the back of the user's eye 10. To compensate for hyperopia, a corrective lens 19 having dual convex sides is worn on (contact lens) or near (eye glasses) the user's eye 10 in order to provide a convergent refractive power that causes the light from display 13 to be focused properly on the user's retina at the back of the eye.

Figure 2B:
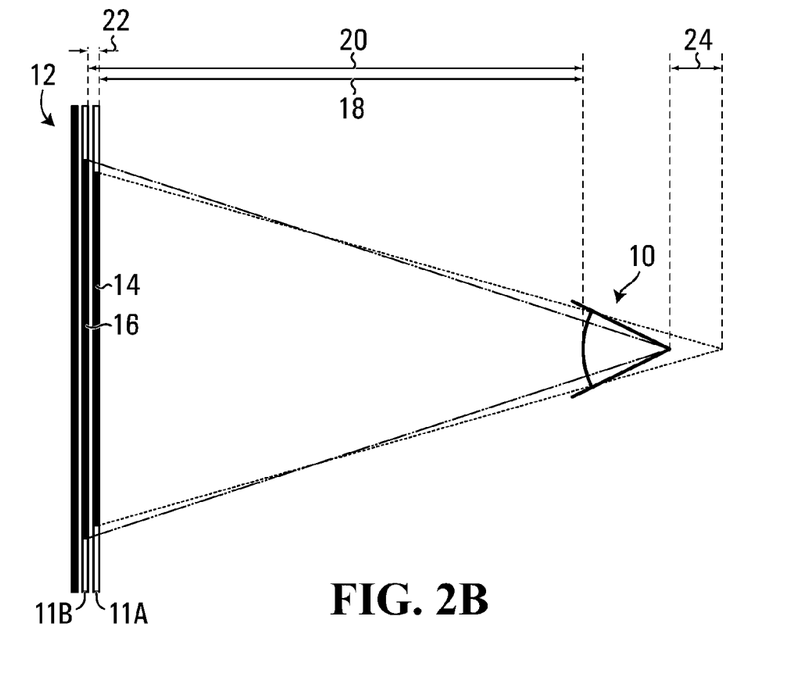
FIG. 2B is a profile view of an image display configured to compensate for hyperopia in accordance with an embodiment of the present disclosure.

FIG. 2B is a profile view of an image display 12 configured to compensate for an eye prescription indicative of hyperopia in accordance with an embodiment of the present disclosure. As noted above with respect to FIG. 2A, without the corrective lens 19, light from display 13 will be focused at a point behind the user's eye 10. FIG. 2B illustrates an example of how a display 12 having a front display plane 11A and back display plane 11B separated by a distance 22 can be operated in order to compensate for hyperopia when a user is not wearing their corrective eyewear. In FIG. 2B, respective versions 14 and 16 of an image element are displayed on the front display plane 11A and the back display plane 11B respectively of display 12 based on a visual adjustment factor such that the respective versions 14 and 16 of the image element differ in at least one of line weight, transparency, and in some cases light intensity, in a manner that causes the user's eye 10 to focus on the version 14 of the image element displayed on the front display plane 11A, while still perceiving the version 16 of the image element displayed on the rear display plane 11B. For example, the respective versions 14 and 16 of the image element may be displayed such that the version 14 of the image element is substantially transparent yet maintains enough detail to cause the eye to focus upon it, e.g. by increasing the line weight of its boundaries, while also decreasing the line weight and potentially maintaining or increasing the opacity/transparency of the version 16 of the image element displayed on the back display plane 11B of the display 12. In some embodiments, the transparency of the version 14 of the image element displayed on the front display plane 11A of the display 12 is 85-95% transparent.

In some embodiments, the visual adjustment factor is based, at least in part, on eye correction prescription information.

In some embodiments, the user may be prompted to supply eye correction prescription information, and a focal length correction is determined based on spherical correction information included in the eye correction prescription information. Spherical correction is often specified in terms of dioptres. An example of an equation relating spherical correction (in dioptres) to the properties of a user's corrective eyewear is given by:

$$\frac{1}{f} = (n-1)\left[\frac{1}{R_1} - \frac{1}{R_2} + \frac{(n-1)d}{nR_1R_2}\right],$$

where f is the focal length of the lens, $$\frac{1}{f}$$

is equal to the spherical correction in dioptres, n is the refractive index of the lens material, $R_1$ is the radius of curvature of the lens surface closest to the light source, $R_2$ is the radius of curvature of the lens surface farthest from the light source, and d is the thickness of the lens (the distance along the lens axis between the two surface vertices).

In some embodiments, the respective versions 14 and 16 of the image element displayed on the front display plane 11A and the back display plane 11B are displayed with relative scaling with respect to one another based on the focal length correction and the distance between the display 12 and the user's eye 10, which may be considered as either the distance 18 to the front display plane 11A or the distance 20 to the back display plane 11B, so that the respective image elements 14 and 16 appear as if they were of the same size but offset by a distance equal to the focal length correction when viewed at the distance between the display and the user's eyes. This relative scaling mimics the perceived difference in size of an object at different distances.

The relative scaling of the respective versions 14 and 16 of the image element mimics an offset between the image elements that is substantially equal to the focal length correction determined based on the spherical correction of the user's eye prescription information so that the respective version 16 of the image element displayed on the back display plane 11B appears to be behind the respective version 14 of the image element displayed on the front display plane 11A by a distance substantially equal to the focal length correction.

In general, for those embodiments in which the respective versions of an image element are scaled relative to one another, the respective version of the image element that is displayed on the display plane that the eye is intended to be "tricked" into focusing upon is scaled relative to the respective version of the image element displayed on the other display plane, which may be maintained at its original size.

As the user's eye 10 is "tricked" to focus on the respective version 14 of the image element displayed on the front display plane 11A, which, due to the user's hyperopia condition will be improperly focused a distance 24 behind the user's eye, the respective version 16 of the image element displayed on the rear display plane 11B is perceived by the user's eye 10 as an image that is properly focused on the back of the user's eye, which mimics the divergent refractive power of the corrective lens 19 shown in FIG. 2A.

Figure 3A:
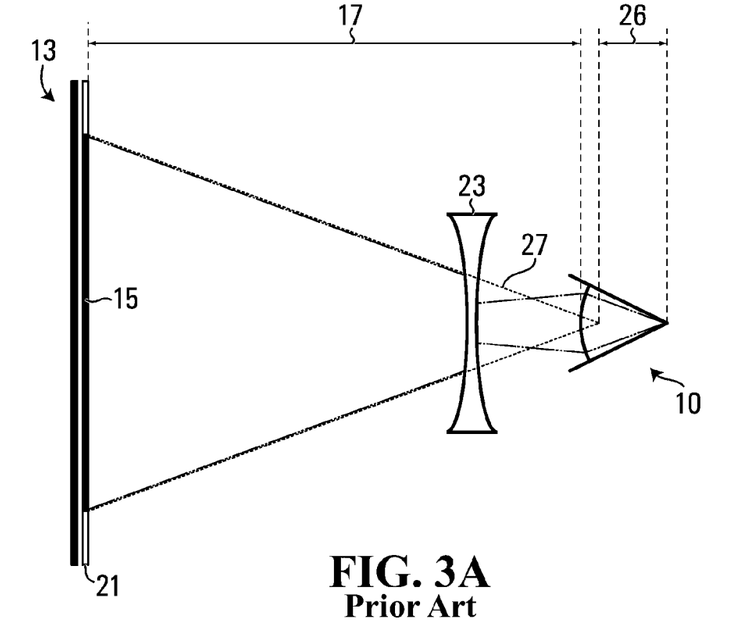
FIG. 3A is a profile view of a conventional image display and a prescription lens configured to compensate for myopia.

FIG. 3A is a profile view of a conventional image display 13 and a divergent prescription lens 23 configured to compensate for myopia. The image display 13 has a single display plane 21 on which an image 15 is displayed. When a user, whose eye is generally indicated at 10 in FIG. 3A, views the image 15 displayed on the display plane 21 of display 13 at a distance 17 from the display, the imperfections in the user's eye 10 that cause myopia cause light from display 13 to be improperly focuses at a distance 26 in front of the user's eye retina, rather than properly focusing the light on the retina at the back of the user's eye 10. To compensate for myopia, a corrective divergent lens 23 having dual concave sides is worn on (contact lens) or near (eye glasses) the user's eye 10 in order to provide a divergent refractive power that causes the light from display 13 to be focused properly on the user's retina at the back of the eye.

Figure 3B:
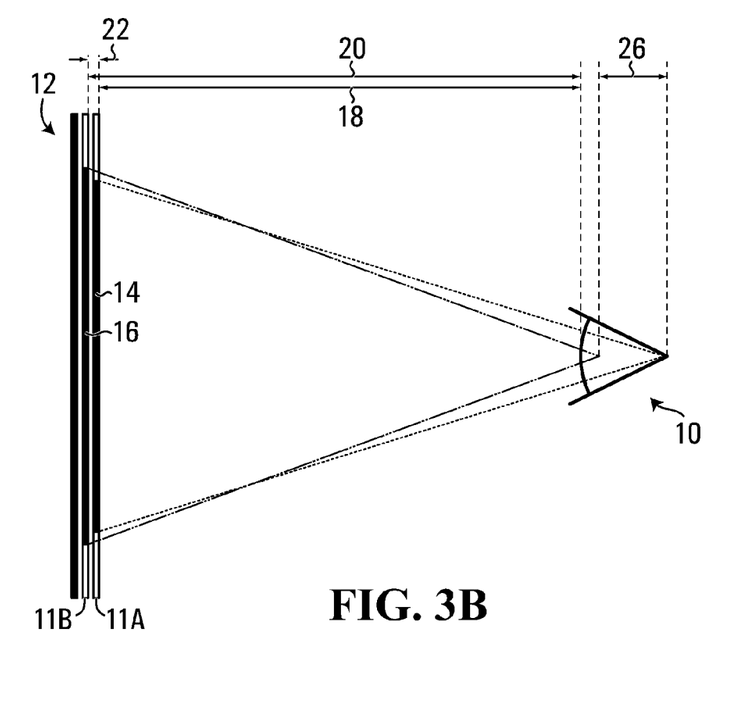
FIG. 3B is a profile view of an image display configured to compensate for myopia in accordance with an embodiment of the present disclosure.

FIG. 3B is a profile view of an image display configured to compensate for myopia in accordance with an embodiment of the present disclosure. As noted above with respect to FIG. 3A, without the corrective divergent lens 23, light from display 13 will be focused at a point in front of the user's eye 10. FIG. 3B illustrates an example of how a display 12 having a front display plane 11A and back display plane 11B separated by a distance 22 can be operated in order to compensate for myopia when a user is not wearing their corrective eyewear. In FIG. 3B, respective versions 14 and 16 of an image element of an image are displayed on the front display plane 11A and the back display plane 11B respectively of display 12 based on a visual adjustment factor such that the respective versions 14 and 16 of the image element differ in at least one of line weight, transparency, and in some cases light intensity, in a manner that causes the user's eye 10 to focus on the respective version 16 of the image element displayed on the rear display plane 11B, while still perceiving the respective version 14 of the image element displayed on the front display plane 11A. This may be done, for example, by displaying the respective versions 14 and 16 of the image element such that they differ in at least one of line weight, transparency and light intensity, so that the respective version 16 of the image element displayed on the back display plane 11B of the display 12 is substantially transparent yet maintains enough detail to cause the eye to focus upon it. In some embodiments, the transparency of the image element on the rear display plane of the display is 85-95% transparent.

As described above, in some embodiments the visual adjustment factor comprises eye correction prescription information from which a focal length correction is determined based on a spherical correction included in the eye correction prescription information. In some embodiment, the user is prompted to provide the eye correction prescription information.

In some embodiments, the respective image elements 14 and 16 of the front display plane 11A and the back display plane 11B are displayed with relative scaling with respect to one another based on the focal length correction and the distance between the display 12 and the user's eye 10, which may be considered as either the distance 18 to the front display plane 11A or the distance 20 to the back display plane 11B, so that the respective versions 14 and 16 of the image element appear as if they were of the same size but offset by a distance equal to the focal length correction when viewed at the distance between the display and the user's eyes.

As the user's eye 10 is "tricked" to focus on the respective version 16 of the image element displayed on the rear display plane 11B, which, due to the user's myopia condition will be improperly focused a distance 26 in front of the user's retina, the respective version 14 of the image element displayed on the front display plane 11A is perceived by the user's eye 10 as an image that is properly focused on the back of the user's eye, which mimics the convergent refractive power of the corrective lens 23 shown in FIG. 3A.

In some embodiments, while the user's eye is "tricked" into focusing on the front display plane or the rear display plane of the display, the line weight and/or transparency of the respective versions of the image element(s) displayed on the other of the planes (front display plane for myopia, rear display plane for hyperopia) is adjusted based on a cylindrical correction indicated by the eye correction prescription information that may be provided, for example, by the user. That is, astigmatic imperfections in the eye may be at least partially compensated for in some embodiments of the present invention.

In some embodiments, a distance measuring sensor (not shown in FIGS. 2B and 3B) is used to measure the distance between the display and the user's eyes.

In some embodiments, the display 12 shown in FIGS. 2B and 3B automatically adjusts the display based on the time of day and/or an elapsed period of inactivity of a device to incorporate the display, such as a mobile device. That is, in some embodiments, displaying a respective version of an image element on each of the front display plane and the back display plane based on a visual adjustment factor such that the respective versions of the image element differ in at least one of line weight and transparency corresponds to the display 12 operating in a compensated display mode, and the display 12 is configured to automatically operate in the compensated display mode based on at least one of time of day and an elapsed period of inactivity. For example, the display may automatically operate in the compensated display mode when first turned on or activated in the morning.

In some embodiments, the display 12 is configured to switch between the compensated display mode and at least one other display mode responsive to user input. In some embodiments, the user input may be selection of a key or button on a user input device such as a keyboard or a mobile device keypad.

In some embodiments, the display is incorporated into a mobile device, such as, for example, the mobile devices that are described later with reference to FIGS. 6 and 7.

A general method for displaying an image in accordance with an embodiment of the present disclosure will now be described with reference to FIG. 4. A more specific embodiment of a method for displaying an image in accordance with the present disclosure is described later for illustrative purposes only with reference to FIG. 5.

Figure 4:
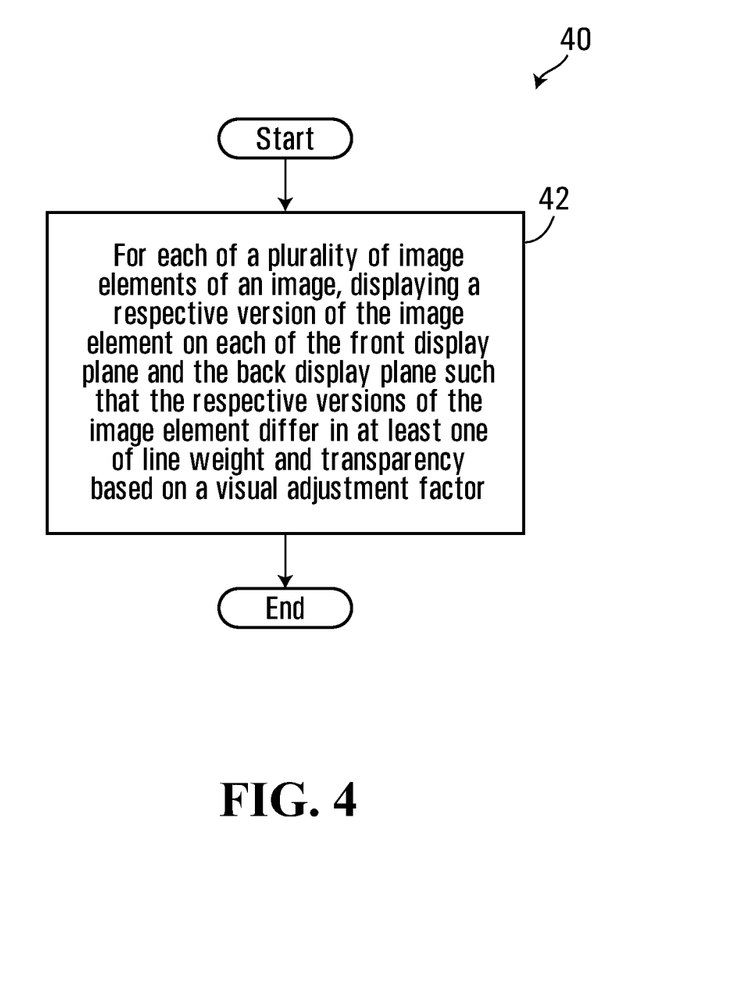
FIG. 4 is a flowchart of a method for displaying based on a visual adjustment factor in accordance with an embodiment of the present disclosure.

FIG. 4 is a flowchart 40 of a method for displaying an image on a display having a front display plane and a back display plane based on a visual adjustment factor in accordance with an embodiment of the present disclosure.

The flowchart 40 includes a method block 42, in which, for each of a plurality of image elements of an image, a respective version of the image element is displayed on each of the front display plane and the back display plane based on a visual adjustment factor, such that the respective versions of the image element differ in at least one of line weight and transparency.

In some embodiments, the difference in at least one of line weight and transparency between the respective versions of the image element displayed on the front display plane and the back display plane based on the visual adjustment factor sets the visual focal length to the display to one of the front display plane and the back display plane while the respective version of the image element displayed on the other one of the front display plane and the back display plane is perceptible.

In some embodiments, the method further comprises adjusting light intensity of at least one of the front display plane and the back display plane based on the visual adjustment factor. Light intensity of an image element can be adjusted, for example, by increasing or decreasing the intensity of the displayed image element or by setting the intensity to a selected setting with or without regard to what the current intensity may be.

In some embodiments, the visual adjustment factor comprises eye correction prescription information. In some embodiments, the visual adjustment factor is a numerical factor. The visual adjustment factor may be expressed as a digital signal or an analog signal or both. In some embodiments, the visual adjustment factor is an absolute measure of something, such as a focal length.

In some embodiments, displaying a respective version of the image element on each of the front display plane and the back display plane based on a visual adjustment factor such that the respective versions of the image element differ in at least one of line weight and transparency comprises: displaying a respective version of the image element on each of the front display plane and the back display plane, such that the visual focal length to the display is set to the front display plane of the display for eye correction prescription information indicative of hyperopia; and displaying a respective version of the image element on each of the front display plane and the back display plane such that the visual focal length to the display is set to the rear display plane of the display for eye correction prescription information indicative of myopia.

In some embodiments, the eye correction prescription information comprises a spherical correction, and the method further comprises: determining a focal length correction based on the spherical correction; and displaying the respective image elements of the front display plane and the back display plane of the display with relative scaling with respect to one another based on the focal length correction and a distance between the display and the user's eyes.

In some embodiments, the method further comprises determining the distance between the display and a user's eyes by measuring the distance with a measuring device.

In some embodiments, the method further comprises prompting for entry of the eye correction prescription information.

In some embodiments, displaying a respective version of the image element on each of the front display plane and the back display plane based on a visual adjustment factor such that the respective versions of the image element differ in at least one of line weight and transparency corresponds to operating in a compensated display mode, the method further comprising automatically operating in the compensated display mode responsive to at least one of: a time of day; and an elapsed period of inactivity of the display.

In some embodiments, displaying a respective version of the image element on each of the front display plane and the back display plane based on a visual adjustment factor such that the respective versions of the image element differ in at least one of line weight and transparency corresponds to operating in a compensated display mode, the method further comprising switching between the compensated display mode and at least one other display mode responsive to user input.

As noted above, FIG. 4 is a flowchart that illustrates a general embodiment of a method for displaying in accordance with the present disclosure. A more specific embodiment of a method for displaying will now be described with reference to FIG. 5.

Figure 5:
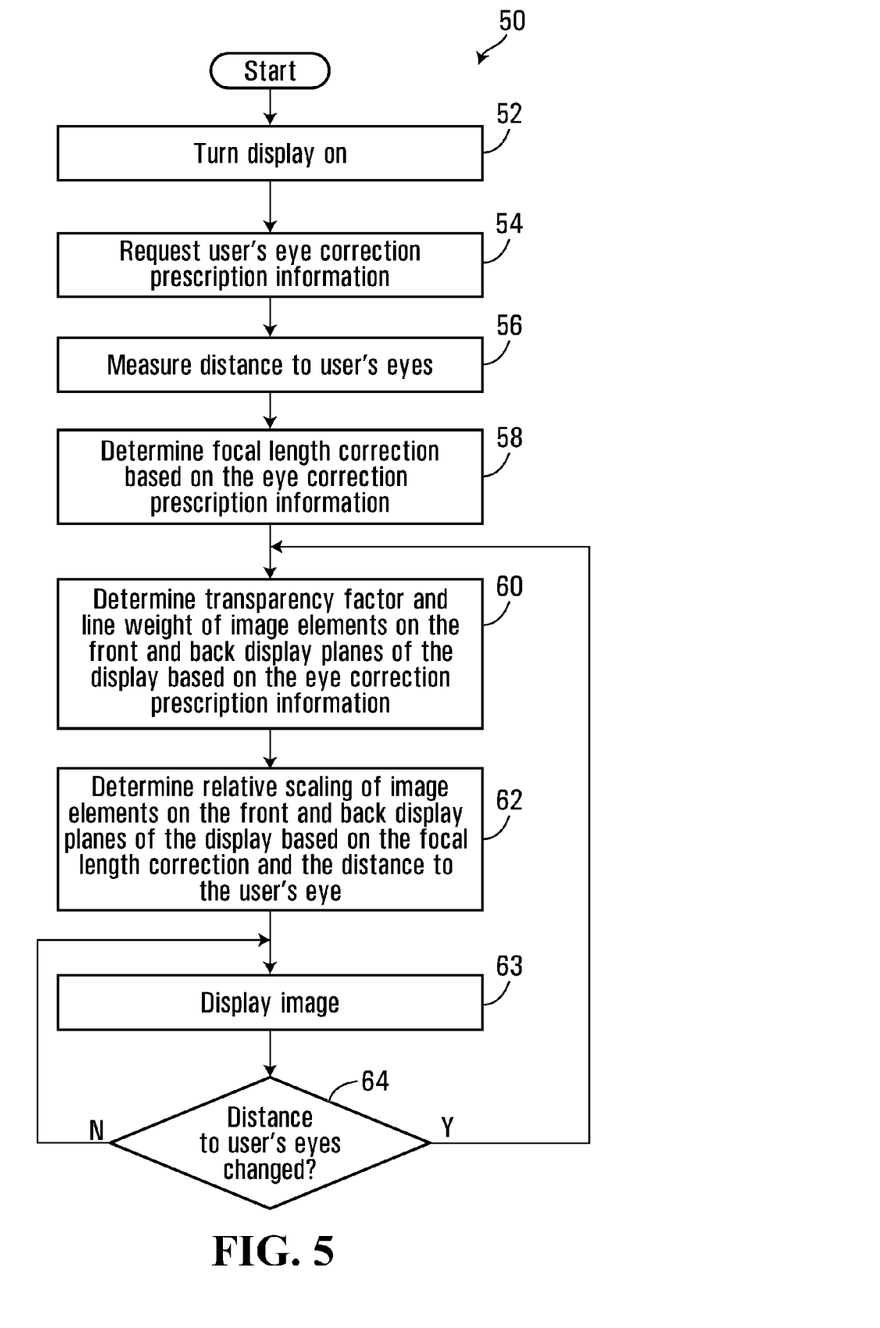
FIG. 5 is a flowchart of a distance to eye compensated method for displaying based on a user's eye prescription in accordance with an embodiment of the present disclosure.

FIG. 5 is a flowchart 50 of a distance to eye compensated method for displaying images on a display having a front display plane and a back display plane based on a user's eye correction prescription information in accordance with an embodiment of the present disclosure.

The method begins at block 52 in which the display is turned on, at which point the method proceeds to block 54.

In block 54, a request for eye prescription information is made to a user and the method proceeds to block 56. The eye prescription information may include a spherical correction and an indication of correction for either myopia or hyperopia. In some embodiments, the eye prescription information also includes cylindrical correction information.

In block 56, the distance between the display and the user's eyes is determined and the method proceeds to block 58. In some embodiments, the distance is measured by a distance measuring sensor incorporated into the same device as the display. The distance may be measured in many possible ways. One example of measuring distance to the user's eyes is to use two cameras for two camera detection where the parallax of the image obtained by the cameras is combined with facial feature recognition software to determine the distance between the display and the eyes of the user. In another embodiment, a laser distance measurement is used to measure the distance to the user's eyes.

In block 58, a visual adjustment factor is determined based on the user's eye prescription information. In the illustrated embodiment, the visual adjustment factor is a focal length correction that is determined based, at least in part, on the user's eye correction prescription information and the method proceeds to block 60. In some embodiments, the focal length correction is determined by using a look up table that maps focal length correction values to radii of curvature that may be determined from a user's eye correction prescription information.

In block 60, a transparency factor and independent line weight of the respective image elements that are to be displayed on the front display plane and the back display plane of the display are determined based on the user's eye correction prescription information, such that the respective versions of image elements displayed on the front display plane and the back display plane differ in at least one of line weight and transparency. The method then proceeds to block 62

In block 62, a relative scaling of respective image elements of the front display plane and the back display plane of the display is determined based on the focal length correction determined in block 58 and the distance between the display and the user's eyes. The relative scaling of image elements on the front display plane of the display relative to corresponding image elements on the rear display plane of the display is performed so that the image elements on the rear display plane appear to be offset behind the corresponding image elements on the front display plane by a distance substantially equal to the focal length correction when viewed at the distance between the user's eyes and the display.

In some embodiments, the relative transparency and line weight of the respective image elements of the planes of the display are adjusted in block 60 based on cylindrical correction information included in the user's eye correction prescription information. For example, in some embodiments the respective image elements of one or both of the display planes are sheared in the direction of the cylindrical correction indicated by the cylindrical correction information.

At block 63, the image, which includes the respective versions of the image elements on the front display plane and the rear display plane of the display are displayed, which depending on the image properties of the respective versions of the image elements displayed on the front display plane and the back display plane, causes focal length to the display to be adjusted to either the front display plane or the rear display plane of the display, as discussed above with reference to FIGS. 2B and 3B.

In some embodiments, as images are displayed, the distance to the user's eyes continues to be monitored at block 64 and if no significant change in the distance is determined, then the images continue to be displayed with the adjusted focal length as described above (N path at block 64). If a change in the distance is determined that would warrant a readjustment of the focal length, then the method returns to block 60 (Y path at block 64) where a new scaling factor is determined based on the focal length correction and the distance to the user's eyes. The amount of change in the distance between the user's eyes and the display that would trigger the Y path at block 64 is an implementation dependent detail.

The method described by the flowchart 50 illustrated in FIG. 5 is merely illustrative of one embodiment of the present disclosure. Other embodiments may include additional steps to the method, omit steps shown in FIG. 5 and/or reorder the steps shown in FIG. 5.

In some embodiments, the method further comprises a block in which, responsive to user input, the display switches between a compensated display mode in which the focal length to the display is adjusted to the front display plane or the back display plane of the display according to steps 54 to 64, and a second display mode in which the focal length to the display is unadjusted.

In some embodiments, the display automatically executes blocks 54 to 64 after turning on in block 52. In some embodiments, a user's eye correction prescription information is stored. In some embodiments, if a user's eye correction prescription information has been previously stored, steps 56 to 64 are automatically executed after block 52 without a prompt for the user's eye correction prescription information at block 54.

Figure 6:
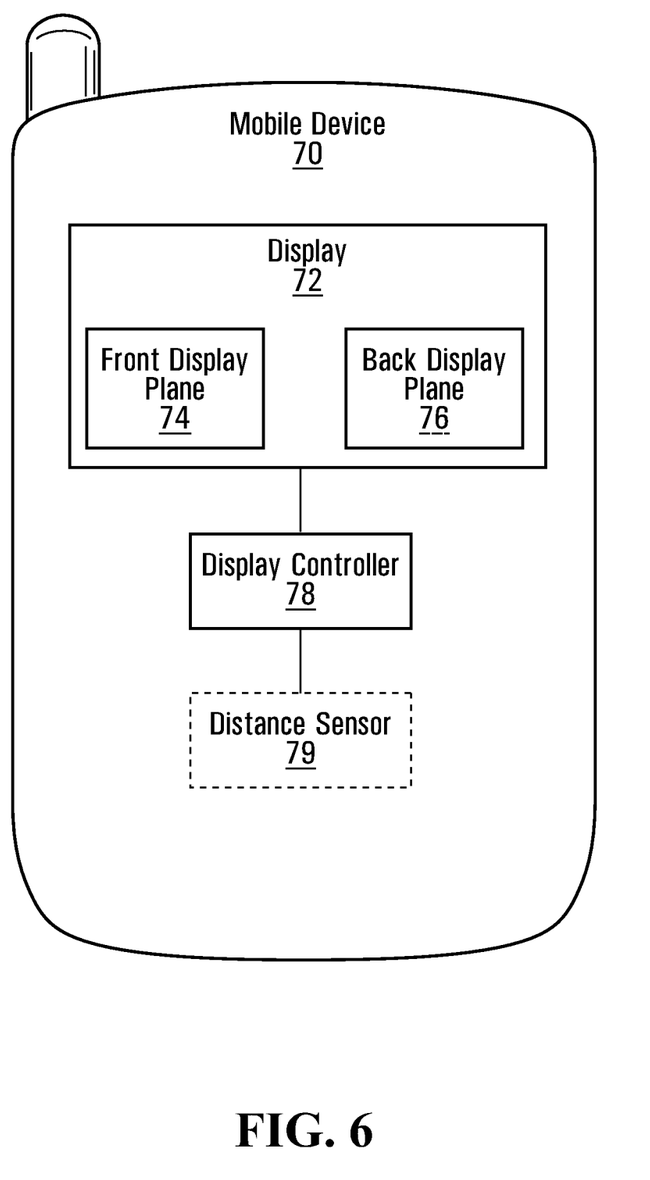
FIG. 6 is a block diagram of a wireless device in accordance with an embodiment of the present disclosure.

Referring now to FIG. 6, shown is a block diagram of a mobile device 70 in accordance with an embodiment of the present disclosure that includes a display 72 and a display controller 78. The mobile device 70 may have other components, but they are not shown for the sake of simplicity.

The display 72 includes a front display plane 74 and a back display plane 76.

The display controller 78 is configured, in a compensated display mode, to control the display 72 to display, for each of a plurality of image elements of an image, a respective version of the image element on each of the front display plane 74 and the back display plane 76 of the display 72 based on a visual adjustment factor such that the respective versions of the image element differ in at least one of line weight and transparency.

In some embodiments, the display controller 78 is configured to control the display 72 to display the respective versions of the image elements such that the difference in at least one of line weight and transparency between the respective versions of the image element displayed on the front display plane 74 and the back display plane 76 based on the visual adjustment factor sets the visual focal length to the display 72 to one of the front display plane 74 and the back display plane 76 while the respective version of the image element displayed on the other one of the front display plane 74 and the back display plane 76 is perceptible.

In some embodiments, the display controller 78 is further configured to adjust light intensity of at least one of the front display plane 74 and the back display plane 76 based on the visual adjustment factor.

In some embodiments, the visual adjustment factor comprises eye correction prescription information, which may, for example, be entered by user of the mobile device via user interface controls (not shown in FIG. 6).

In some embodiments, the display controller 78 is configured to control the display 72 to adjust at least one of the line weight and transparency of the respective versions of the image elements of the front display plane 74 and the back display plane 76 such that the visual focal length to the display 72 is set to the front display plane 74 for eye correction prescription information indicative of hyperopia.

In some embodiments, the display controller 78 is configured to control the display 72 to adjust at least one of the line weight and transparency of the respective versions of the image elements of the front display plane 74 and the back display plane 76 such that the visual focal length to the display 72 is set to the rear display plane 76 for eye correction prescription information indicative of myopia.

In some embodiments, the eye correction prescription information comprises a spherical correction and the display controller 78 is further configured to determine a focal length correction based on the spherical correction and control the display 72 to display the respective versions of the image elements of the front display plane 74 and the back display plane 76 with relative scaling with respect to one another based on the focal length correction and a distance between the display 72 and the user's eyes.

In some embodiments, such as the embodiment illustrated in FIG. 6, the mobile device 70 includes a distance measuring sensor 79 configured to measure the distance between the display 72 and a user's eyes.

In some embodiments, the display controller 78 is further configured to prompt for entry of the eye correction prescription information. Prompting may be done by displaying a message on the display, generating a sound prompt, generating a tactile prompt, e.g. vibration, a combination of two or more of the foregoing mechanisms, or any other mechanisms for alerting the user of the option of entering eye correction prescription information.

In some embodiments, the display controller 78 is further configured to automatically operate in the compensated display mode responsive to a time of day and/or an elapsed period of inactivity of the mobile device 70.

In some embodiments, the display controller 78 is further configured to switch between the compensated display mode and at least one other display mode responsive to user input.

Figure 7:
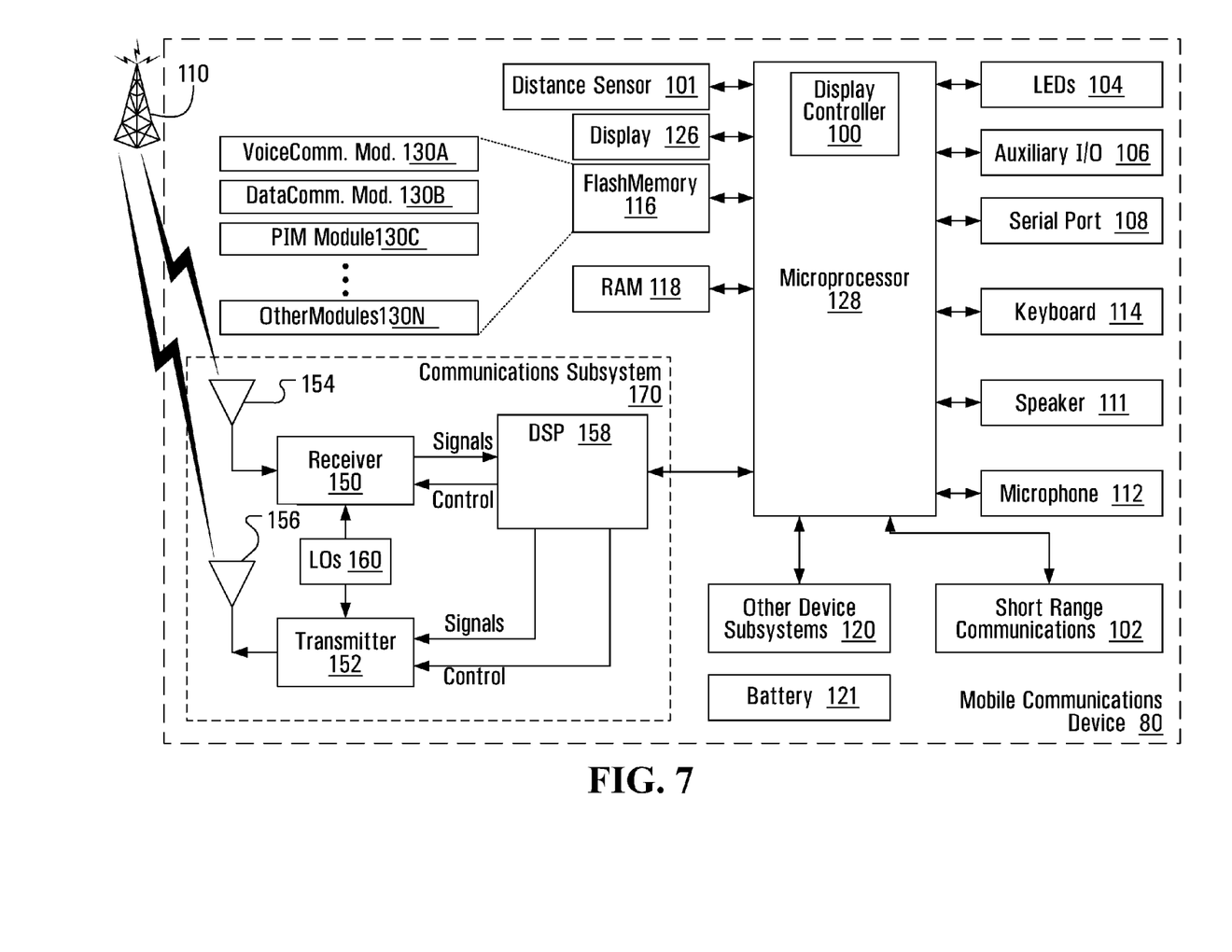
FIG. 7 is a block diagram of another wireless device in accordance with an embodiment of the present disclosure.

Referring now to FIG. 7, shown is a block diagram of another mobile device 80 that may implement any of the methods described herein. It is to be understood that the mobile device 80 is shown with very specific details for example purposes only.

A processing device (a microprocessor 128) is shown schematically as coupled between a keyboard 114 and a display 126. The microprocessor 128 implements a display controller 100 that controls operation of the display 126. Other control functionality implemented by the microprocessor 128 controls overall operation of the mobile device 80, in response to actuation of keys on the keyboard 114 by a user. The mobile device 80 includes a distance sensor 101 and a display 126 having a front display plane and a rear display plane. The distance sensor 101 is configured to measure the distance between the display 126 and a user's eyes. The display controller 100 implements a method for distance to eye compensated displaying of images based on a user's eye prescription information in accordance with the embodiments discussed above with reference to FIGS. 1 to 5. Accordingly, a repetition of the description of the operation of the display method is omitted here.

While the display controller 100 is shown as being part of the microprocessor 128 in FIG. 7, in some embodiments the functionality of the display controller may be implemented separately from the microprocessor or as some combination of hardware, software and firmware.

In some embodiments, the distance sensor 101 may be implemented with a laser-based measurement sensor and/or a dual camera distance detection system, as described earlier.

The mobile device 80 has a housing that may be elongated vertically, or may take on other sizes and shapes (including clamshell housing structures). The keyboard 114 may include a mode selection key, or other hardware or software for switching between text entry and telephony entry.

In addition to the microprocessor 128, other parts of the mobile device 80 are shown schematically. These include: a communications subsystem 170; a short-range communications subsystem 102; the keyboard 114, the distance sensor 101 and the display 126, along with other input/output devices including a set of LEDS 104, a set of auxiliary I/O devices 106, a serial port 108, a speaker 111 and a microphone 112; as well as memory devices including a flash memory 116 and a Random Access Memory (RAM) 118; and various other device subsystems 120. The mobile device 80 may have a battery 121 to power the active elements of the mobile device 80. The mobile device 80 is in some embodiments a two-way radio frequency (RF) communication device having voice and data communication capabilities. In addition, the mobile device 80 in some embodiments has the capability to communicate with other computer systems via the Internet.

Operating system software executed by the microprocessor 128 is in some embodiments stored in a persistent store, such as the flash memory 116, but may be stored in other types of memory devices, such as a read only memory (ROM) or similar storage element. In addition, system software, specific device applications, or parts thereof, may be temporarily loaded into a volatile store, such as the RAM 118. Communication signals received by the mobile device 80 may also be stored to the RAM 118.

The microprocessor 128, in addition to its operating system functions, enables execution of software applications on the mobile device 80. A predetermined set of software applications that control basic device operations, such as a voice communications module 130A and a data communications module 130B, may be installed on the mobile device 80 during manufacture. In addition, a personal information manager (PIM) application module 130C may also be installed on the mobile device 80 during manufacture. The PIM application is in some embodiments capable of organizing and managing data items, such as e-mail, calendar events, voice mails, appointments, and task items. The PIM application is also in some embodiments capable of sending and receiving data items via a wireless network 110. In some embodiments, the data items managed by the PIM application are seamlessly integrated, synchronized and updated via the wireless network 110 with the device user's corresponding data items stored or associated with a host computer system. As well, additional software modules, illustrated as another software module 130N, may be installed during manufacture.

Communication functions, including data and voice communications, are performed through the communication subsystem 170, and possibly through the short-range communications subsystem 170. The communication subsystem 170 includes a receiver 150, a transmitter 152 and one or more antennas, illustrated as a receive antenna 154 and a transmit antenna 156. In addition, the communication subsystem 170 also includes a processing module, such as a digital signal processor (DSP) 158, and local oscillators (LOs) 160.

The specific design and implementation of the communication subsystem 170 is dependent upon the communication network in which the mobile device 80 is intended to operate. For example, the communication subsystem 170 of the mobile device 80 may be designed to operate with the Mobitex™, DataTAC™ or General Packet Radio Service (GPRS) mobile data communication networks and also designed to operate with any of a variety of voice communication networks, such as Advanced Mobile Phone Service (AMPS), Time Division Multiple Access (TDMA), Code Division Multiple Access CDMA, Personal Communications Service (PCS), Global System for Mobile Communications (GSM), etc. Other types of data and voice networks, both separate and integrated, may also be utilized with the mobile device 80.

Network access may vary depending upon the type of communication system. For example, in the Mobitex™ and DataTAC™ networks, mobile devices are registered on the network using a unique Personal Identification Number (PIN) associated with each device. In GPRS networks, however, network access is typically associated with a subscriber or user of a device. A GPRS device therefore typically has a subscriber identity module, commonly referred to as a Subscriber Identity Module (SIM) card, in order to operate on a GPRS network.

When network registration or activation procedures have been completed, the mobile device 80 may send and receive communication signals over the communication network 110. Signals received from the communication network 110 by the receive antenna 154 are routed to the receiver 150, which provides for signal amplification, frequency down conversion, filtering, channel selection, etc., and may also provide analog to digital conversion. Analog-to-digital conversion of the received signal allows the DSP 158 to perform more complex communication functions, such as demodulation and decoding. In a similar manner, signals to be transmitted to the network 110 are processed (e.g., modulated and encoded) by the DSP 158 and are then provided to the transmitter 152 for digital to analog conversion, frequency up conversion, filtering, amplification and transmission to the communication network 110 (or networks) via the transmit antenna 156.

In addition to processing communication signals, the DSP 158 provides for control of the receiver 150 and the transmitter 152. For example, gains applied to communication signals in the receiver 150 and the transmitter 152 may be adaptively controlled through automatic gain control algorithms implemented in the DSP 158.

In a data communication mode, a received signal, such as a text message or web page download, is processed by the communication subsystem 170 and is input to the microprocessor 128. The received signal is then further processed by the microprocessor 128 for an output to the display 126, or alternatively to some other auxiliary I/O devices 106. A device user may also compose data items, such as e-mail messages, using the keyboard 114 and/or some other auxiliary I/O device 106, such as a touchpad, a rocker switch, a thumb-wheel, or some other type of input device. The composed data items may then be transmitted over the communication network 110 via the communication subsystem 170.

In a voice communication mode, overall operation of the device is substantially similar to the data communication mode, except that received signals are output to a speaker 111, and signals for transmission are generated by a microphone 112. Alternative voice or audio I/O subsystems, such as a voice message recording subsystem, may also be implemented on the mobile device 80. In addition, the display 126 may also be utilized in voice communication mode, for example, to display the identity of a calling party, the duration of a voice call, or other voice call related information.

The short-range communications subsystem 102 enables communication between the mobile device 80 and other proximate systems or devices, which need not necessarily be similar devices. For example, the short-range communications subsystem may include an infrared device and associated circuits and components, or a Bluetooth™ communication module to provide for communication with similarly-enabled systems and devices.

It should be understood that as used herein, terms such as coupled, connected, electrically connected, in signal communication, and the like may include direct connections between components, indirect connections between components, or both, as would be apparent in the overall context of a particular embodiment. The term coupled is intended to include, but not be limited to, a direct electrical connection.

The foregoing description includes many detailed and specific embodiments that are provided by way of example only, and should not be construed as limiting the scope of the present invention. Alterations, modifications and variations may be effected to the particular embodiments by those of skill in the art without departing from the scope of the invention, which is defined solely by the claims appended hereto.

The invention claimed is:

1. A method for displaying information using a display to at least partially compensate for vision impairment of a user, the display having a front display plane and a back display plane, the method comprising:
   receiving eye correction prescription information including spherical correction information;
   determining a focal length correction based on the spherical correction information; and
   for each of a plurality of image elements of an image, displaying a respective version of the image element on each of the front display plane and the back display plane based on a visual adjustment factor such that the respective versions of the image element differ in at least one of line weight and transparency and have relative scaling with respect to one another so that:
   the respective versions of the image element appear of same size but offset by a distance equal to the focal length correction when viewed from a viewing distance; and
   one of the respective versions of the image element causes the user's eyes to focus so that the other respective version of the image element is perceived by the user's eyes as being focused in a manner mimicking the refractive power of a corrective lens based on the spherical correction information.

2. The method of claim 1, wherein the difference in at least one of line weight and transparency between the respective versions of the image element displayed on the front display plane and the back display plane based on the visual adjustment factor sets the visual focal length to the display to one of the front display plane and the back display plane while the respective version of the image element displayed on the other one of the front display plane and the back display plane is perceptible.

3. The method of claim 2, further comprising adjusting light intensity of at least one of the front display plane and the back display plane based on the visual adjustment factor.

4. The method of claim 2, wherein displaying a respective version of the image element on each of the front display plane and the back display plane based on a visual adjustment factor such that the respective versions of the image element differ in at least one of line weight and transparency comprises:
   displaying a respective version of the image element on each of the front display plane and the back display plane, such that the visual focal length to the display is set to the front display plane of the display for eye correction prescription information indicative of hyperopia; and
   displaying a respective version of the image element on each of the front display plane and the back display plane such that the visual focal length to the display is set to the rear display plane of the display for eye correction prescription information indicative of myopia.

5. The method of claim 2, wherein the viewing distance comprises a distance between the display and the user's eyes.

6. The method of claim 5, further comprising determining the distance between the display and the user's eyes by measuring the distance with a measuring device.

7. The method of claim 1, further comprising prompting for entry of the eye correction prescription information.

8. The method of claim 1, wherein displaying a respective version of the image element on each of the front display plane and the back display plane based on a visual adjustment factor such that the respective versions of the image element differ in at least one of line weight and transparency corresponds to operating in a compensated display mode, the method further comprising automatically operating in the compensated display mode responsive to at least one of:
   a time of day; and
   an elapsed period of inactivity of the display.

9. The method of claim 1, wherein displaying a respective version of the image element on each of the front display plane and the back display plane based on a visual adjustment factor such that the respective versions of the image element differ in at least one of line weight and transparency corresponds to operating in a compensated display mode, the method further comprising switching between the compensated display mode and at least one other display mode responsive to user input.

10. A device for displaying information to at least partially compensate for vision impairment of a user, the device comprising:
 a display having a front display plane and a back display plane; and
 a display controller that is configured to:
  receiving eye correction prescription information including spherical correction information,
  determine a focal length correction based on the spherical correction information, and
  in a compensated display mode, control the display to display, for each of a plurality of image elements of an image, a respective version of the image element on each of the front display plane and the back display plane of the display based on a visual adjustment factor such that the respective versions of the image element differ in at least one of line weight and transparency and have relative scaling with respect to one another so that:
  the respective versions of the image element appear of same size but offset by a distance equal to the focal length correction when viewed from a viewing distance; and
  one of the respective versions of the image element causes the user's eyes to focus so that the other respective version of the image element is perceived by the user's eyes as being focused in a manner mimicking the refractive power of a corrective lens based on the spherical correction information.

11. The device of claim 10, wherein the display controller is configured to control the display to display the respective versions of the image elements such that the difference in at least one of line weight and transparency between the respective versions of the image element displayed on the front display plane and the back display plane based on the visual adjustment factor sets the visual focal length to the display to one of the front display plane and the back display plane while the respective version of the image element displayed on the other one of the front display plane and the back display plane is perceptible.

12. The device of claim 11, wherein the display controller is further configured to adjust light intensity of at least one of the front display plane and the back display plane based on the visual adjustment factor.

13. The device of claim 11, wherein the display controller is configured to:
 control the display to adjust at least one of the line weight and transparency of the respective versions of the image elements of the front display plane and the back display plane such that the visual focal length to the display is set to the front display plane for eye correction prescription information indicative of hyperopia; and
 control the display to adjust at least one of the line weight and transparency of the respective versions of the image elements of the front display plane and the back display plane such that the visual focal length to the display is set to the rear display plane for eye correction prescription information indicative of myopia.

14. The device of claim 11, wherein the viewing distance comprises a distance between the display and the user's eyes.

15. The device of claim 14, further comprising a distance measuring sensor configured to measure the distance between the display and the user's eyes.

16. The device of claim 10, wherein the display controller is further configured to prompt for entry of the eye correction prescription information.

17. The device of claim 10, wherein the display controller is further configured to automatically operate in the compensated display mode responsive to at least one of:
 a time of day; and
 an elapsed period of inactivity of the device.

18. The device of claim 10, wherein the display controller is further configured to switch between the compensated display mode and at least one other display mode responsive to user input.

19. The device of claim 10, wherein the device is a mobile device.

* * * * *